United States Patent [19]

Burks, Jr. et al.

[11] Patent Number: 4,533,473

[45] Date of Patent: Aug. 6, 1985

[54] PROCESS FOR TREATING LIQUID CHLORINATED HYDROCARBON WASTES CONTAINING IRON

[75] Inventors: William M. Burks, Jr., Yorktown Heights, N.Y.; Elliott P. Doane, Monroe, Conn.; Ramsey G. Campbell, Berkeley; Emilio S. Velez, Richmond, both of Calif.

[73] Assignee: Stauffer Chemical Company, Westport, Conn.

[21] Appl. No.: 576,243

[22] Filed: Feb. 2, 1984

Related U.S. Application Data

[63] Continuation of Ser. No. 378,368, May 14, 1982, abandoned.

[51] Int. Cl.$^3$ .............................................. C02F 1/64
[52] U.S. Cl. .................................... 210/754; 210/912
[58] Field of Search ............... 210/754, 912, 749, 799; 570/238, 262, 263

[56] References Cited

U.S. PATENT DOCUMENTS

| | | | |
|---|---|---|---|
| 3,095,368 | 6/1963 | Bieber et al. | 208/252 |
| 3,115,528 | 12/1963 | Benner et al. | 260/652 |
| 3,647,895 | 3/1972 | Fruhwirth et al. | 260/650 R |
| 3,691,239 | 9/1972 | Hackett et al. | 260/652 P |
| 3,839,463 | 10/1974 | Cohn | 260/612 D |
| 4,307,261 | 12/1981 | Beard et al. | 570/262 |

FOREIGN PATENT DOCUMENTS

| | | |
|---|---|---|
| 1939391 | 3/1977 | Fed. Rep. of Germany . |
| 2900521 | 7/1980 | Fed. Rep. of Germany . |
| 41-13606 | 7/1966 | Japan . |
| 1380497 | 1/1975 | United Kingdom . |

Primary Examiner—Thomas Wyse
Attorney, Agent, or Firm—Joel G. Ackerman

[57] ABSTRACT

Iron, such as ferric chloride, and other metallic impurities, contained in liquid chlorinated hydrocarbon waste streams, is removed by treatment of such streams with dilute aqueous mineral acid.

21 Claims, 6 Drawing Figures

PROCESS FOR TREATING LIQUID CHLORINATED HYDROCARBON WASTES CONTAINING IRON

This is a continuation of application Ser. No. 378,368, filed May 14, 1982, now abandoned.

BACKGROUND AND PRIOR ART

This invention relates to the treatment of liquid chlorinated hydrocarbon streams, particularly waste streams, to remove ferric iron and optionally other metallic impurities contained therein, and more particularly for the treatment of such streams containing comparatively large amounts of ferric iron, ranging on the order of from about 200–300 ppm up to 2% by weight or higher.

A number of valuable chlorinated hydrocarbons such as methyl chloride, methylene chloride, chloroform, carbon tetrachloride, 1,2-dichloroethane, 1,1-dichloroethane, 1,1,2-trichloroethane, trichloroethylene, perchloroethylene, ethyl chloride 1,1,1-trichloroethane, allyl chloride, chlorobutenes, chloroprene, and mono- and polychlorinated benzenes, are conventionally produced by processes in which in one or more steps ferric chloride is employed as a catalyst or is formed by corrosion of steel or steel alloy equipment by process chemicals including chlorine and hydrogen chloride. In such processes, there are generated one or more waste streams containing, in addition to the desired product or products, more highly chlorinated or oligomeric by-products (generally referred to as "heavy ends"). Such streams are generally obtained by separation of the desired product from by-products in one or more distillation columns. These heavy ends streams generally contain substantial amounts of iron compounds (usually in the form of ferric chloride) which represent primarily ferric chloride used as a catalyst in one or more upstream processes steps, and often also some resulting from corrosion. In general, these chlorinated hydrocarbon streams or heavy ends are ultimately disposed of by thermal or catalytic incineration or oxidation, for instance, in a high temperature thermal incinerator or by fluidized bed catalytic incineration or oxidation. Optionally, prior to incineration the heavy ends streams may first be concentrated in a tar still or other equipment, from which additional desired products may be recovered as overhead and a more concentrated heavy ends as bottoms product.

For instance, such heavy ends streams are formed in commercial facilities for the production of vinyl chloride from ethylene and chlorine, and may emanate from one or more units in such a plant.

In such a commercial plant, ethylene is reacted with chlorine, in a liquid phase reactor (the liquid medium being primarily 1,2-dichloroethane together with other chlorinated hydrocarbons such as 1,1,2-trichloroethane) with ferric chloride being employed as a chlorination catalyst. The chlorination may be carried out at temperatures of between about 40° and 60° C. (so-called "low temperature" chlorination) with a comparatively low concentration of ferric chloride catalyst being employed (generally approximately 50 ppm), or at a temperature at or above the normal boiling point of 1,2-dichloroethane, i.e., 83.5° C. or above (generally up to about 110°–120° C., so-called "high temperature" chlorination). Ferric chloride is also utilized as a catalyst here, but in substantially larger amounts.

If the chlorination is of the "high temperature" type, the 1,2-dichloroethane is vaporized in the chlorination reactor and fractionally distilled in an associated fractionated column, following which it is passed into a pyrolysis or cracking furnace in which it is thermally dehydrochlorinated to produce vinyl chloride and hydrogen chloride. Optionally, the dehydrochlorination may be carried out catalytically. The gaseous products leaving the dehydrochlorination step are quenched, usually by direct contact with a liquid, usually recycled 1,2-dichloroethane, and passed to product separation in which vinyl chloride, hydrogen chloride, and uncracked 1,2-dichloroethane are ultimately recovered.

If the chlorination is of the "low temperature" type, 1,2-dichloroethane is continuously removed from the chlorination reactor and eventually distilled in a series of fractionating columns. These columns are generally divided into two sections, termed "light ends" and "heavy ends" distillation. In the light ends column or columns, low boiling impurities are separated from the dichloroethane, which is removed as a bottoms product and passed into the heavy ends column or columns. In the latter, dichloroethane is taken out as an overhead product and higher boiling impurities removed as bottoms product. The heavy ends are usually concentrated in a "tar still", which may be a kettle or type of distillation apparatus, or by vacuum distillation, with th residue being passed to incineration or oxidation.

In such processes there are several primary sources of waste streams containing chlorinated hydrocarbons and also containing ferric chloride which may be treated by the process of the present invention. These streams include:

(a) a purge stream taken off the ethylene chlorination reactor to prevent the undesirable build-up of high boiling by-products;

(b) the bottoms product from the heavy ends distillation section;

(c) the residue contained in the concentration apparatus after separation of desired product 1,2-dichloroethane; and (d) residues remaining after purification and recovery of 1,2-dichloroethane recovered unconverted from the pyrolysis furnace or other dehydrochorination step.

The above mentioned waste streams will contain a number of chlorinated hydrocarbons including for example 1,2-dichloroethane, 1,1-dichloroethane, dichloroethylenes, trichlorethylene, perchloroethylene, 1,1,2-trichloroethane, 1,1,1-trichloroethane (methylchloroform), 1,1,2,2-tetrachloroethane; penta- and hexachloroethanes, and chlorobutadienes such as chloroprene.

Processes for the production of other chlorinated hdyrocarbons, for instance, products such as perchloroethylene, 1,1,2-trichloroethane, ethyl chloride, allyl chloride, 1,1-dichloroethane, chlorinated benzenes and various chloromethanes, will also involve the production of waste streams similar to those mentioned above and containing various chlorinated hydrocarbons together with ferric chloride, which may be utilized in the process as a chlorination or hydrochlorination catalyst, or result from corrosion.

In general, as mentioned above, it is common practice to concentrate the various waste streams, producing a residual product comprising the heavier chlorinated hydrocarbons, ferric chloride or other iron compounds and carbon, which is then generally disposed of by one or more means of incineration. However, the presence of amounts of ferric chloride or other iron salts in the residues to be incinerated can produce operating difficulties, and even serious problems.

In thermal incineration, the waste streams or residues are burned in a combustion furnace which is often equipped with one or more waste heat boilers. Ferric chloride or other iron compounds contained in the wastes may be converted under incinerator conditions to iron oxides which coat and cause pluggage of the waste heat boilers, requiring either extensive cleaning or replacement.

In processes in which the wastes are catalytically incinerated or oxidized, they are passed to a fluidized bed of catalytic material supported on an inert particulate support and burned at high temperatures. An overly high amount of iron can accumulate in the catalyst bed, requiring removal or replacement of the catalytic material on an undesirably frequent schedule.

Similar problems may also be caused by the presence of salts of other metals, notably copper or nickel, from other catalysts used in the facitilities or from corrosion of equipment.

In some plants, the difficulties of operating an incinerator (whether thermal or catalytic) to burn waste streams containing high amounts of ferric chloride has resulted in the only feasible method of incineration being that conducted at sea by incinerator ships such as the well known "vulcanus". Such techniques are expensive and do not provide a means for recovering chlorine values from the waste. Furthermore, there are only several such ships functioning today, so that it is necessary to store wastes for a lengthy period of time and schedule use of these ships quite far in advance.

It is an objective of this invention, therefore, to provide a process for the treatment of such chlorinated hydrocarbon waste streams containing relatively heavy or high boiling chlorinated hydrocarbons together with substantial amounts of ferric chloride or other iron salts, to remove substantial portions of the iron component so as to make such streams more amenable for conventional incineration.

The prior art discloses a number of techniques for removal of ferric or other iron-containing materials from various chlorinated hydrocarbons. In most cases, however, the prior art is concerned with removal of such contaminants from streams containing primarily 1,2-dichloroethane or other desirable principal products.

Thus, for instance, U.S. Pat. No. 3,691,239 discloses that 1,2-dichloroethane containing iron can be treated with an adsorbent such as a clay or clay-related material, preferably alumina. U.S. Pat. No. 3,115,528 discloses steam distillation with ammonia to precipitate iron as ferric hydroxide. U.S. Pat. No. 3,647,895 involves the use of an anhydrous monoalkanolamine to remove iron impurities. British Pat. No. 1,380,497 performs this operation by adsorbing the iron-containing impurities on charcoal. A similar operation is performed in German Pat. No. 1,939,391.

It has been a practice in commercial vinyl chloride plants to treat 1,2-dichloroethane (produced by chlorination and/or oxychlorination) with dilute acid to remove iron-containing impurities and other undesirable products from the stream prior to passing it through light ends and/or heavy ends distillation. Such streams, emanating primarily from the "low temperature" type of chlorination, generally contain about 50 ppm ferric chloride. The acid solution is then neutralized and disposed of in the usual fashion. Such a process is disclosed, for instance, in Japanese Patent Publication No. 13606/1966.

In a "balanced process" for the production of vinyl chloride, there is additionally incorporated an oxychlorination process unit in which ethylene is reacted with air or oxygen and hydrogen chloride gas recovered from the effluent of the pyrolysis furnace. The principal products of this reaction comprise 1,2-dichloroethane and water, and the product stream may also include a small amount of unreacted ethylene and hydrogen chloride. This product stream, which emanates from the oxychlorination section in the gaseous form, is generally at least partially condensed into a mixture of 1,2-dichloroethane and water.

A dichloroethane product may be combined with the 1,2-dichloroethane produced from "low temperature" ethylene chlorination, thus at the same time effectuating the acid wash of the latter with the aqueous solution of hydrogen chloride produced in the oxychlorination process. The aqueous acid-containing portion is then phase separated from the organic layer, neutralized as mentioned above, and disposed in the customary fashion, while the organic layer containing primarily 1,2dichloroethane is neutralized and passed to the distillation section.

SUMMARY OF THE INVENTION

It has now been found that liquid waste streams containing higher boiling chlorinated hydrocarbons and substantial amounts of metallic contaminants, particularly ferric chloride, may be treated to remove a major portion of the metallic contaminant by contact with a dilute aqueous solution of a mineral acid which contains from about 0.1 to about 10 percent by weight of acid and which is mixed with the waste stream to be treated in a volume ratio of dilute acid to organic material contained in the waste stream of at least about 1:1. Generally, the contaminant is dissolved in the aqueous acid, however, depending on the nature of the waste stream and the metallic contaminant, an emulsion may be formed which may be easily broken. The process is conducted at ambient temperature.

DETAILED DESCRIPTION OF THE INVENTION

In general one or more of the waste streams mentioned above is contacted with a dilute aqueous solution of a mineral acid, preferably hydrochloric acid. This solution will contain from about 0.1 up to about 10 weight percent of acid (e.g., hydrogen chloride), preferably from about 2 to about 10 weight percent. The amount of acid utilized is at least about 1 volume and preferably from about 1 to about 3 volumes, per volume of waste stream (total organic). The process is generally carried out at ambient temperatures, which may be room temperature or somewhat above. The stream being treated may comprise one or more of the types of chlorinated hydrocarbon waste streams mentioned above, and will generally have a ferric chloride content ranging from about 200–300 ppm upward to 2% or more by weight.

The removal of ferric chloride or other iron-containing contaminants from such waste streams by treatment with dilute acids is rendered even more effective if the waste stream is filtered prior to contact with the acid. This removes particulate material, which greatly reduces the tendency to form an emulsion when the stream is contacted with dilute acid, and of course, makes phase separation of the resulting aqueous/organic mixture much easier. Filtration will also remove rust or iron scale which may originate from corrosion of equipment.

Even should an emulsion form, it has been found that treatment according to this invention creates emulsions which may be readily broken by passing the treated material through a filter and coalescer, optionally with the addition of a filter aid, or by centrifugation. The treated mixture is then separated into organic and aqueous phases. The aqueous phase is neutralized, and passed through waste disposal in a conventional manner. The organic phase is then sent for further processing, depending on its content.

Figure 1:
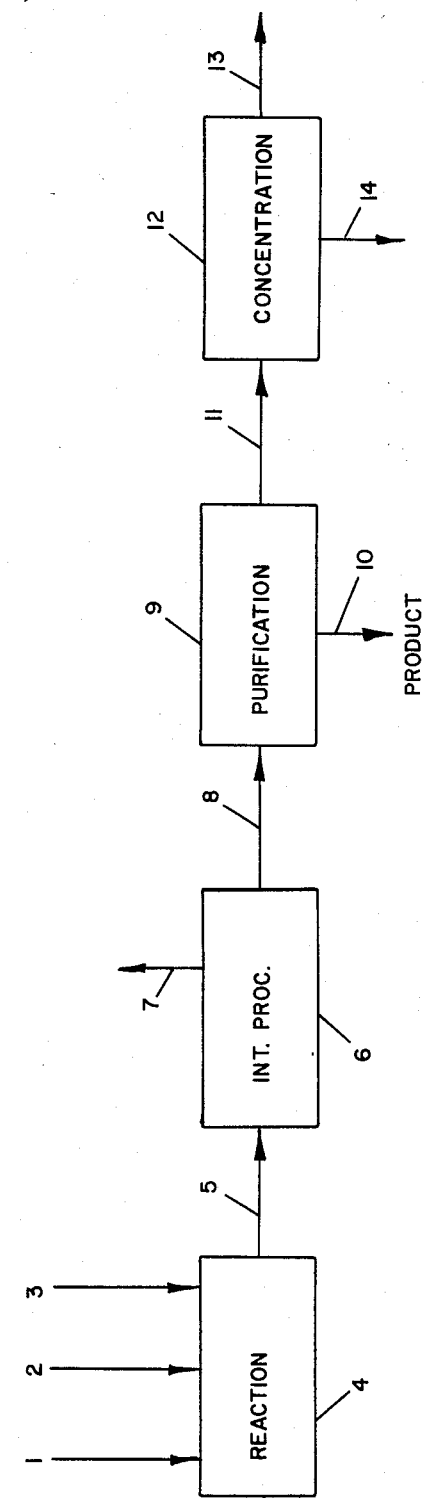
FIG. 1 depicts a typical general process diagram for production of chlorinated hydrocarbons, including the concentration of heavy ends produced in the process.

FIG. 1 depicts, for background, a typical generalized process diagram for production of chlorinated hydrocarbons, including the concentration of heavy ends produced in the process.

The processes described in FIG. 1 may be those utilized for production of any of a number of desirable chlorinated hydrocarbons, including production of 1,2-dichloroethane by chlorination or oxychlorination of ethylene; production of vinyl chloride by dehydrochlorination of 1,2-dichloroethane; production of 1,1-dichloroethane by chlorination or oxychlorination of ethylene; production of vinylidene chloride by dehydrochlorination of 1,1-dichloroethane; production of ethyl chloride by hydrochlorination of ethylene; production of higher chlorinated ethanes such as 1,1,1-trichloroethane, 1,1,2-trichloroethane, and tetrachloroethanes by additive chlorination of 1,2-dichloroethane; production of trichloroethylene and/or perchloroethylene, for instance by oxychlorination of 1,2-dichloroethane; production of allyl chloride by oxychlorination of propylene; production of chlorobutenes and/or chloroprene by oxychlorination, chlorination, and/or dehydrochlorination of various butanes; production of mono- and/or polychlorinated benzenes such as chlorobenzene, dichlorobenzene, etc., by chlorination or oxychlorination of benzene; production of chloromethanes including methyl chloride, methylene chloride, chloroform and/or carbon tetrachloride, by chlorination and/or oxychlorination of methane, optionally mixed with one or more chloromethanes, notably methyl chloride; production of methyl chloride by hydrochlorination of methanol. Alternatively, the process may be one for production of other chlorinated hydrocarbons such as mono- or polychlorinated biphenyls, and various chlorofluoro- or chlorobromo- hydrocarbons.

Referring to FIG. 1, there is introduced into a general reaction section 4, several feed streams. Stream 1 is generally a hydrocarbon and/or chlorinated hydrocarbon to be reacted. Stream 2 is a chlorination or hydrochlorination agent such as chlorine and/or hydrogen chloride. Stream 3 may be another reactant such as air and/or oxygen for utilization in an oxychlorination process.

The reaction products are conveyed via line 5 into an intermediate processing section 6 in which the products are treated by one or more steps such as quenching, condensation, washing with acid and/or water, neutralization, and drying. Liquid and/or gaseous wastes are withdrawn in line 7. The thus treated products are then conveyed via line 8 into a purification or distillation section 9 which comprises one or more distillation or fractionation columns for separating the desired product or products from impurities. The desired product or products are removed in line 10. "Heavy ends," that is, impurities generally boiling higher than the desired products, are taken off in line 11. This stream will usually contain a portion of the desired product or products in addition to the heavy ends. Stream 11 is passed into a concentration section 12, which will comprise one or more vessels such as kettles, often referred to by the term "tar stills", or optionally vacuum distillation columns, or other equipment utilized for the concentration of the higher boiling impurities. Any desirable chlorationed hydrocarbon product which is recovered is removed in line 14 and returned to the main process for further purification as necessary. From the concentration section there is removed a waste stream in line 13 which is then passed to a thermal incinerator or catalytic incinerator or oxidizing section for incineration or combustion.

Figure 2:
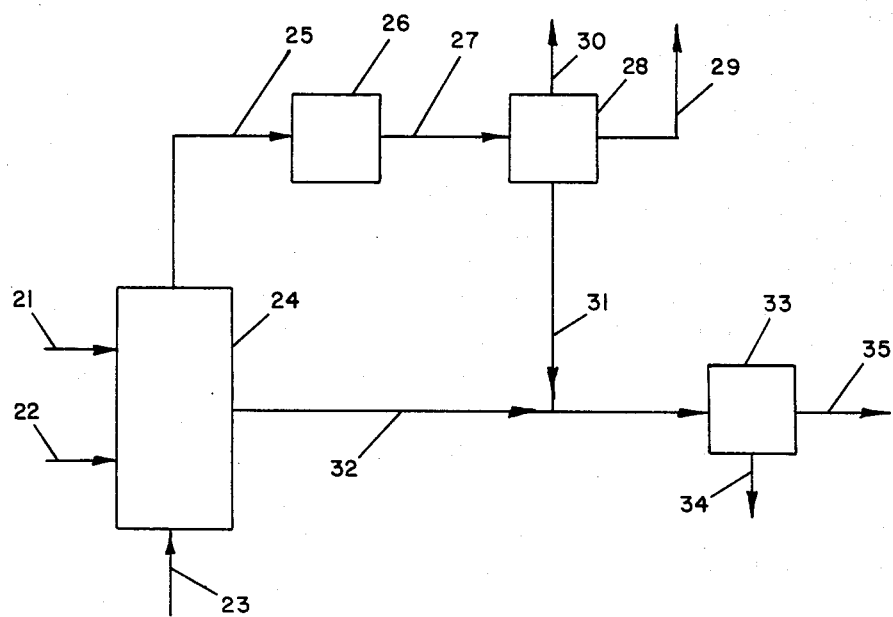
FIG. 2 depicts a typical flowsheet for production of 1,2-dichloroethane by chlorination of ethylene.

FIG. 2 depicts a typical flowsheet for the production of 1,2-dichloroethane by chlorination of ethylene. As mentioned previously, the chlorination may be conducted at either "high temperature" or "low temperature."

In FIG. 2, ethylene in line 21, chlorine in line 22, and optionally recycle make-up liquid in line 23 are introduced into a reactor generally indicated as 24, in which the ethylene and chlorine react to product 1,2-dichloroethane. Some processes conduct chlorination of ethylene in the vapor phase, in which case no make-up liquid need be introduced, but the majority of such processes are carried out in the liquid phase. The liquid constitutes primarily 1,2-dichloroethane and/or 1,1,2-trichloroethane, and contains ferric chloride catalyst. Reactor 24 may be a tank or vessel-type reactor and, in the case of "high temperature" chlorination is preferably a circulating-loop reactor, such as described, for instance, in British Pat. No. 1,422,303 of Stauffer Chemical Company.

Product 1,2-dichloroethane is removed from reactor 24 in line 25 and introduced into a distillation section generally indicated as 28. In the case of "low temperature" chlorination, the 1,2-dichloroethane in line 25 is generally neutralized in a container 26 before being introduced into distillation section 28 via line 27.

In the "low temperature" chlorination process, distillation section 28 generally contains a plurality of distillation columns for removing "light ends" (impurities boiling below 1,2-dichloroethane) and "heavy ends" (impurities boiling above 1,2-dichloroethane) from the dichloroethane product. The light ends are taken off in line 30 and passed downstream for further processing (not shown). The purified 1,2-dichloroethane is removed from distillation section 28 in line 29 and either recovered as product or passed downstream for further processing, such as oxychlorination or chlorination to more highly chlorinated ethanes, or dehydrochlorination to produce vinyl chloride.

Heavy ends are removed from distillation section 28 in line 31 and generally passed into a heavy ends concentration section 33, which may comprise one or more kettles or tar stills, or vacuum distillation columns. Some additional 1,2-dichloroethane will be recovered from the concentration section 33 and removed via line 34, generally being sent for purification such as by distillation. The concentrated heavy residues, comprising chlorinated hydrocarbons boiling higher than 1,2-dichloroethane, such as 1,1,2-trichloroethane, tetrachloroethane and penta- and hexachloroethanes, and also containing from about 15 to about 55% of 1,2-dichloroethane, are removed from the concentration section in line 35 and are sent to thermal incineration or catalytic incineration or oxidation. This stream will generally contain up to about 2000 ppm ferric chloride in the case of "low temperature" chlorination, and up to 2% or more ferric chloride by weight in "high tempratrure" chlorination.

In the case of "high temperature" chlorination, distillation section 28 usually comprises a single fractionation column associated directly with reactor 24 which is fed directly with 1,2-dichloroethane in line 25. This fractionation column may also be used to purify 1,2-dichloroethane obtained from sources other than the chlorination reactor.

There is also removed from the chlorination reactor, particularly in "high temperature" processes, a purge stream 32, which contains the heavy ends as well as ferric chloride. In the case of "high temperature" chlorination, the heavy ends stream 31 from distillation section 28 may feed directly back into the chlorination reactor 24, and heavy ends are removed in the purge stream 32. This purge stream is generally also fed through the concentration section 33.

Figure 3:
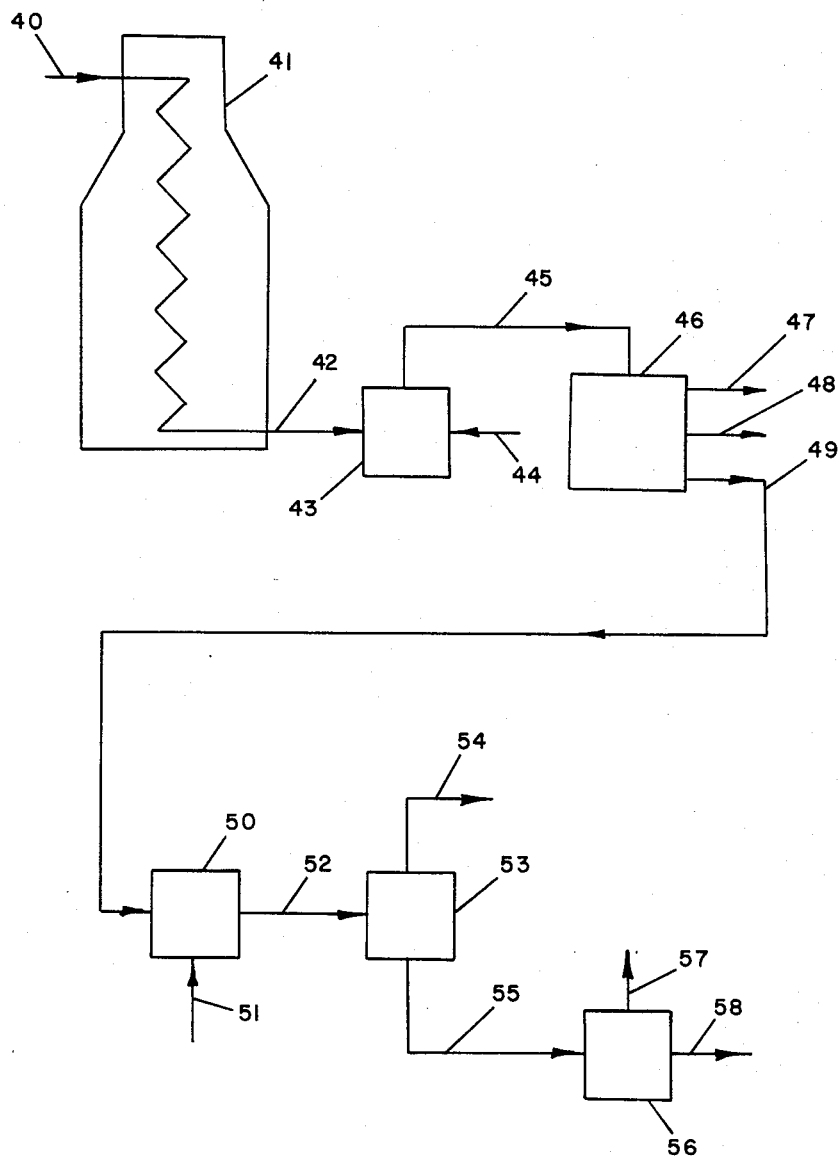
FIG. 3 depicts a typical flowsheet for pyrolysis of 1,2-dichloroethane to vinyl chloride, and recovery and purification of unpyrolyzed 1,2-dichloroethane.

FIG. 3 depicts a typical flowsheet for a process for pyrolysis of 1,2-dichloroethane to vinyl chloride, with recovery and purification of unpyrolyzed 1,2-dichloroethane.

In FIG. 3, a stream comprising essentially 1,2-dichloroethane, and optionally one or more cracking promoters, such as carbon tetrachloride, is introduced via line 40 into a pyrolysis or cracking furnace 41 in which it is thermally dehydrochlorinated to product an effluent containing primarily vinyl chloride, hydrogen chloride, and unpyrolyzed dichloroethane. The effluent is removed in line 42 and introduced into a quench column 43 in which it is quenched by contact with a liquid, usually recycled dichloroethane, introduced, for instance, in line 55. An overhead stream comprising 1,2-dichloroethane, vinyl chloride, and hydrogen chloride is passed via line 45 to a distillation or purification 46. Generally, such a distillation section will contain two or more columns for separation of the 1,2-dichloroethane, vinyl chloride and hydrogen chloride, respectively. The vinyl chloride is removed in line 47 and recovered as product, or passed downstream for further purification if necessary. Hydrogen chloride is removed in line 48 and passed downstream for further treatment (not shown). 1,2-Dichloroethane which has not been converted in the dehydrochlorination section is removed in line 49. If this stream is to be recycled to the pyrolysis furnace via line 40, or for use elsewhere in a vinyl chloride plant, it is preferably treated with chlorine introduced via line 51 into a vessel 50, to chlorinate undesirable by-products such as chloroprene. The treated 1,2-dichloroethane is removed in line 52 and introduced into a distillation or purification section 53. This section contains one or more distillation columns for removing light ends and heavy ends from the dichloroethane. Purified dichloroethane is removed in line 54 and may be recycled to the pyrolysis furnace in line 40.

Heavy ends are removed from distillation section 53 in line 55 and passed to a concentration section 56, which as before, may contain one or more kettles or tar stills or vacuum distillation columns. Additional product 1,2-dichloroethane may be recovered from the concentration section in line 57 and returned to the purification section for further processing. A concentrated heavy ends stream comprising heavily chlorinated ethanes, such as 1,1,2-trichloroethane, chlorinated butanes, and from about 15 to abut 55% of 1,2-dichloroethane, is recovered in line 58 and passed downstream to incineration or oxidation. This stream may contain appreciable amounts of ferric chloride, ranging prhaps from 300 to 2000 ppm, as well as other iron salts and other metallic impurities, originating from corrosion in the equipment.

Figure 4:
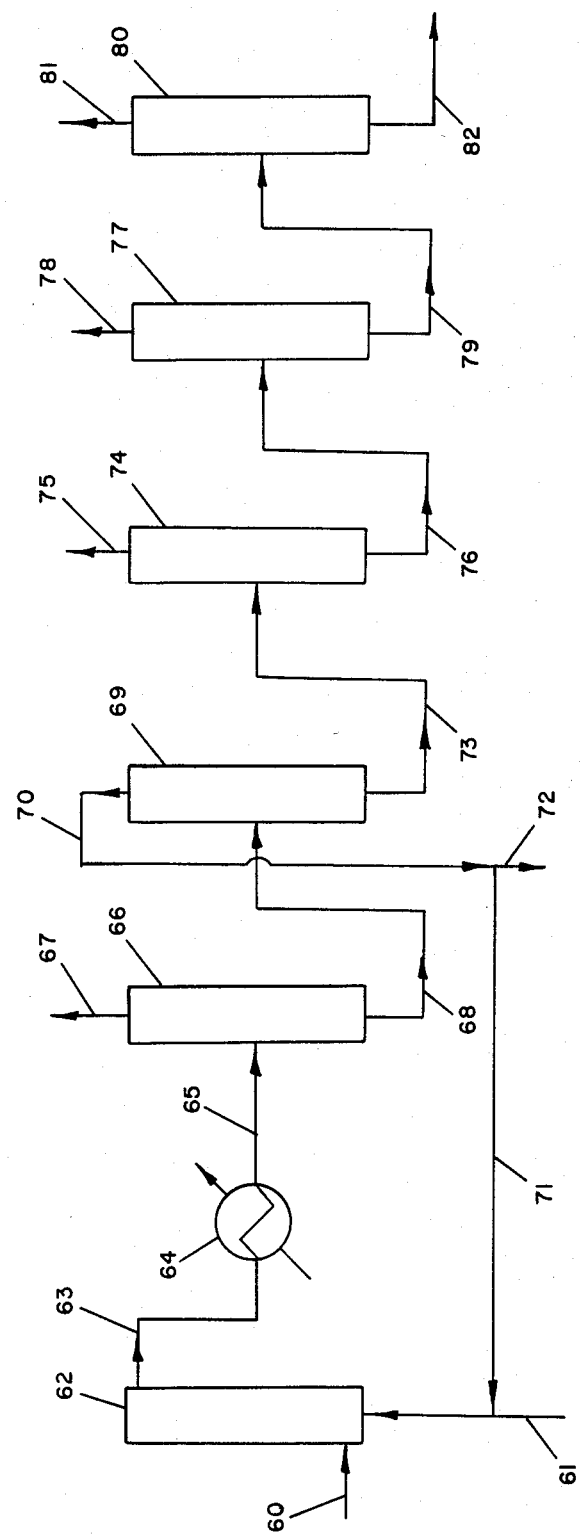
FIG. 4 depicts a typical flowsheet for production of chloromethanes.

FIG. 4 depicts a typical flowsheet for production of chloromethanes by chlorination of a feed comprising methane and/or methyl chloride.

According to FIG. 4 there are introduced into a chlorination reactor 62 a stream comprising methane and/or methyl chloride in line 61, and chlorine in line 60. Reaction is carried out in the presence of a catalyst, generally cupric chloride but possibly also ferric chloride, at temperatures usually ranging from about 250° to about 500° C.

A product stream comprising a mixture of chloromethanes is removed in line 63, cooled in a condenser or cooler 64, and passed through a series of distillation columns via line 65. In column 66, hydrogen chloride is removed as overhead in line 67 and a mixed chloromethane stream as bottoms product in line 68. The mixed chloromethane stream is introduced into methyl chloride column 69 from which methyl chloride is recovered as overhead in ine 70 and either recycled in line 71 to be fed to the chlorination reactor 62, or recovered via line 72 as product. The bottoms from the methyl chloride column in line 73 are introduced into methylene chloride column 74 from which methylene chloride is recovered as overhead in line 75.

The bottoms from this column are removed in line 76 and introduced into chloroform column 77 from which chloroform is recovered overhead in line 78. The bottoms from the chloroform column are removed in line 79 and introduced into a carbon tetrachloride column 80. Carbon tetrachloride is recovered as overhead in line 81 and a heavy ends stream, comprising materials boiling higher than the chloromethanes, recovered in line 82. This stream will contain heavy ends such as trichloroethylene, perchloroethylene, hexachloroethane, as well as small amounts of chloromethanes, and from about 300 to about 2000 ppm of ferric chloride, resulting from corrosion of the equipment. As this stream is already concentrated in heavy ends, it is generally not sent to further concentration.

Figure 5:
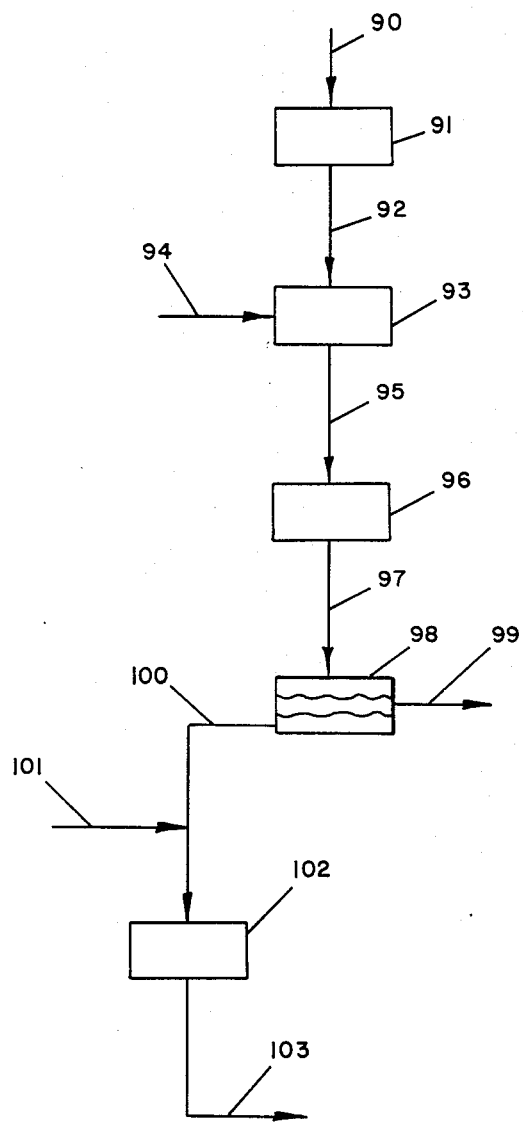
FIG. 5 depicts a general process for treating chlorinated hydrocarbon waste streams according to this invention.

FIG. 5 depicts a generalized process for treating chlorinated hydrocarbon waste streams according to the invention described herein. Referring to the generalized diagram of FIG. 1, the process may be utilized to treat waste streams obtained from a heavy ends concentration section, in line 13, or heavy ends obtained from a purification section, in line 11, prior to their being introduced into the concentration section.

With reference to FIG. 5, a waste stream in line 90 is fed to the process of this invention. This stream may be, for instance:

- with reference to FIG. 2, a concentrated waste stream in line 35, a heavy ends stream from a distillation section in line 31, and/or a purge stream removed from a chlorination reactor in line 32;
- with reference to FIG. 3, a concentrated heavy ends stream removed in line 58, or a heavy ends stream removed from a distillation section in line 55;
- with reference to FIG. 4, the heavy ends stream, already concentrated, in line 82;
- or, with reference to any other processes described herein, any other concentrated heavy ends stream, or heavy ends stream recovered from a distillation or fractionation section.

The waste stream or streams in line 90 are preferably passed through a filter 91 to remove solid particulate material, and then passed via line 92 into an acid treatment tank 93 in which they are contacted with a dilute aqueous solution of a mineral acid which contains from about 0.1 to about 10 percent by weight of acid, preferably from about 2 to about 10 weight percent, introduced via line 94. The mineral acid may be, for instance, hydrochloric, sulfuric, or nitric acid, and is preferably hydrochloric acid. The amount of acid utilized to treat the waste streams is at least about one volume of acid per volume of organic material in the wastes.

The upper limit on the amount of acid utilized is generally dictated by practical operation conditions, including availability of materials and size of equipment. Generally, more than 3 volumes of acid per volume of organic material is not required. Depending on the nature of the waste stream, and the iron content, it may be advantageous to use greater volumes of acid to minimize emulsion problems.

The liquid from tank 93 is then removed via line 95 and may be passed through a coalescer and filter, or centrifuge, 96, if necessary to break any emulsion which may have formed. Then, the liquid material is conveyed via line 97 to a phase separation tank 98 in which separation into aqueous and organic phases occurs. The aqueous (acidic) phase is withdrawn from tank 98 via line 99 and passed to neutralization and waste disposal facilities (not shown). The organic material, now freed from most of the ferric chloride or other salts, is removed in line 100. As this stream is now slightly acidic, it is neutralized, for instance, by introduction of gaseous ammonia in line 101 and passed through a filter 102 to remove ammonium chloride. The treated and neutralized waste stream is then passed via line 103 to thermal or catalytic incineration or oxidation.

It has been found that treatment of the waste stream or streams in this manner either produces no emulsion of the material in tank 93 or an emulsion which is very readily broken by simply passing through a coalescer and filter, or centrifuge, 96.

In some cases an emulsion will not be formed between the organic and aqueous phases, and the liquid mixture from tank 93 may be passed directly to the separation tank 98.

Similarly, the pre-treatment filtration in filter 90 is not necessary in all cases, but it is advisable in many cases, particularly when treating residues from heavy ends concentration or a purge from a "high temperature" chlorinator, as solid particles are more likely to be found in these streams, and their removal can serve to minimize the likelihood of forming an emulsion in the acid wash tank 93.

Figure 6:
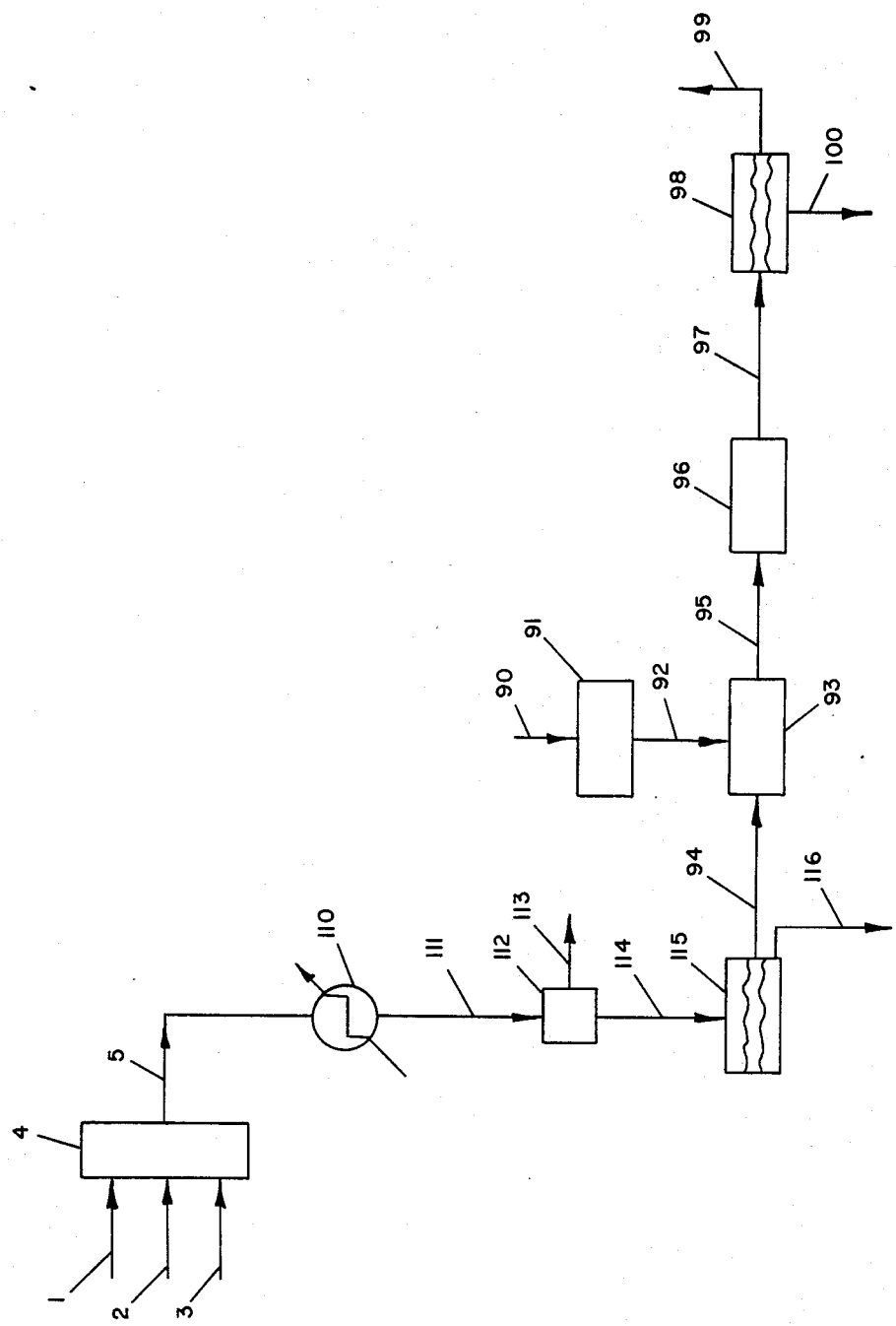
FIG. 6 depicts an embodiment of the invention in combination with a process which produces an aqueous solution of hydrogen chloride.

In FIG. 6 there is depicted an embodiment of the invention in combination with a process which produces a dilute aqueous solution of hydrogen chloride. In this embodiment, the dilute aqueous hydrochloric acid produced in the process is used to treat one or more chlorinated hydrocarbon waste streams also produced in the process, or even in another process conducted in the same general locality.

Processes which produce chlorinated hydrocarbon waste streams and also produce dilute aqueous hydrochloric acid generally comprise processes for the oxychlorination of various hydrocarbons or chlorinated hydrocarbons. These include, for instance, oxychlorination of ethylene to 1,2-dichloroethane; oxychlorination of 1,2-dichloroethane to produce trichloroethylene, perchloroethylene, and higher chlorinated products from the dichloroethane; oxychlorination of propylene to produce allyl chloride; and oxychlorination of methane and/or methyl chloride to produce chloromethanes. Also, processes such as hydrochlorination of methanol to produce methyl chloride will produce chlorinated hydrocarbon waste streams as well as dilute aqueous hydrochloric acid.

In accordance with FIG. 6, one or more of the above processes is carried out in a reactor generally designated as 4 which is fed by streams 1, 2, and/or 3. For instance, in an oxychlorination process, stream 1 may be a hydrocarbon such as ethylene or propylene, stream 2 may be hydrogen chloride and/or chlorine, and stream 3, air and/or oxygen. The reaction products are removed via line 5, cooled or condensed in one or more heat exchangers 110 and passed via line 111 to a liquid/vapor separator 112. Gaseous materials are removed via line 113 and passed downstream for further treatment (not shown). A liquid effluent containing primarily the desired chlorinated hydrocarbon product (for instance 1,2-dichloroethane or allyl chloride) together with water of reaction and some dissolved unreacted hydrogen chloride is removed in line 114. The liquid material in line 114 is introduced into a tank or vessel 115 in which separation occurs between aqueous and organic phases. The organic phase, comprising the desired chlorinated hydrocarbon product, is removed in line 116 and passed downstream for further processing such as purification (not shown). The aqueous phase, comprising water and dissolved hydrogen chloride, is removed from tank 115 in line 94.

The aqueous hydrochloric acid in line 94 is then introduced into a tank 93 and used to treat waste streams originally introduced into the system via line 90, as in FIG. 5.

In one embodiment of a process as shown in FIG. 6, the plant in which the wastes are produced is a commercial facility for the production of vinyl chloride from ethylene and chlorine by what is generally termed a "balanced process". In such a plant, the ethylene feed is divided into two portions. One portion is converted to 1,2-dichloroethane by oxychlorination with hydrogen chloride and oxygen and/or air employing a fixed or fluidized bed catalytic material. The products of such a reaction are generally recovered as shown in FIG. 6. Optionally, the gaseous effluent in line 5 may be washed with water prior to cooling, to extract unreacted hydrogen chloride as dilute aqueous hydrochloric acid.

A second portion of the ethylene is reacted with chlorine as shown generally in FIG. 2 to produce 1,2-dichloroethane. The 1,2-dichloroethane produced in the oxychlorination and chlorination sections is purified, either in separate purification sections or in a combined one, and then introduced into a pyrolysis furnace for dehydrochlorination to vinyl chloride as generally shown in FIG. 3. Hydrogen chloride produced in the pyrolysis section is generally recycled to the oxychlorination reactor to serve as feed, while unconverted 1,2-dichloroethane from the pyrolysis section is generally recycled to the chlorination reactor as make-up liquid medium.

In such a process, a dilute aqueous hydrochloric acid stream results from the oxychlorination section, while various heavy ends are produced in the distillation sections of the plant. The heavy ends streams are concentrated in one or more stills or vacuum distillation columns before being thermally or catalytically incinerated or oxidized. It is advantageous in such a a process to utilize the hydrochloric acid from the oxychlorination step to treat either the concentrated heavy ends, or the heavy ends as obtained from the distillation columns, according to the process of FIG. 6, before the wastes are passed to incineration or oxidation.

In general, the process of this invention is best utilized to treat the heavy ends streams obtained from the concentration section (stream 13 of FIG. 1). However, the process may also be used to remove ferric chloride or other metallic impurities from the heavy ends streams obtained from the purification sections, in line 11 of FIG. 1. In such case, the treated waste stream would be neutralized, for instance, with gaseous ammonia as shown in FIG. 5, so that the concentration section need not be constructed of acid resistant materials.

EXAMPLE

A bottoms stream 46 was taken off a heavy ends column of a "low temperature" ethylene chlorination process as depicted in FIG. 2. The bottoms stream contained 1,2-dichloroethane, 1,1,2-trichloroethane, tetrachloroethanes, pentachloroethanes, chlorinated butenes and/or butanes, and "tars", and contained 27 ppm ferric chloride.

An amount of anhydrous ferric chloride was added to raise the total contents to approximately 1 weight percent ferric chloride. The material was then passed through a 15–25 micron filter, to remove solid particles.

The filtered organic material was then contacted with an equal volume of 1.0N aqueous hydrogen chloride solution (approximately 3.6 weight percent HCl). The two liquids were maintained in contact for a period of about 1–2 minutes. The total material was then passed through a glass wool coalescer to break any emulsion which had formed, and was then separated into aqueous and organic phases.

The organic phase was analyzed for ferric chloride content.

Analyses of five samples treated in this manner showed that the ferric chloride had been reduced from an initial concentration of 1 weight percent, to a concentration of between about 25 and about 55 ppm. Such a concentration is too low to produce any adverse effect in the operation of either thermal or catalytic incinerators used for the incineration of waste streams from vinyl chloride processes.

What is claimed is:

1. A process for removing a metallic contaminant from a liquid waste stream containing one or more chlorinated hydrocarbons, said waste stream emanating from one or more of the following sources: a purge stream from a hydrocarbon chlorination reactor, a bottoms product from a heavy ends distillation section, a residue contained in a concentration apparatus after separation of a desired chlorinated hydrocarbon product, and a residue remaining after purification and recovery of a desired chlorinated hydrocarbon product from a dehydrochlorination process, said process comprising contacting said waste stream with at least about one volume, per volume of organic material in the waste stream, of a dilute aqueous solution of a mineral acid containing from about 0.1 to about 10% by weight of acid, and separating the resulting aqueous and organic phases.

2. A process according to claim 1 in which the metallic contaminant comprises an iron salt.

3. A process according to claim 2 in which the iron salt comprises ferric chloride.

4. A process according to claim 1 in which the mineral acid is hydrochloric acid.

5. A process according to claim 1 in which the waste stream is contacted with from about 1 to about 3 volumes of acid, per volume of organic material.

6. A process according to claim 1 in which the aqueous solution of hydrochloric acid contains from about 2 to about 10 percent by weight of hydrogen chloride.

7. A process according to claim 1 in which the volume ratio of acid to liquid waste stream is about 1:1.

8. A process according to claim 1 further comprising filtering solid particulate material from the waste stream prior to contacting it with the acid.

9. A process according to claim 1 further comprising passing the mixture of liquid waste stream and dilute acid through a filter and coalescer, prior to separating the organic and aqueous phases.

10. A process according to claim 1 in which the waste stream is obtained from a process for production of 1,2-dichloroethane by chlorination of ethylene.

11. A process according to claim 1 in which the waste stream is obtained from a process for production of vinyl chloride by dehydrochlorination of 1,2-dichloroethane.

12. A process according to claim 1 in which the waste stream is obtained from a process for production of one or more chloromethanes by chlorination of a feed comprising methane and/or methyl chloride.

13. A process according to claim 1 in which the acid is a dilute aqueous solution of hydrogen chloride obtained from a process for production of a chlorinated hydrocarbon by oxychlorination of a hydrocarbon or chlorinated hydrocarbon.

14. In a process for the production of vinyl chloride from ethylene and chlorine, in which the ethylene is reacted with oxygen and/or air and hydrogen chloride in an oxychlorination section to produce 1,2-dichloroethane, ethylene is reacted with chlorine in a chlorination section to produce additional 1,2-dichloroethane, the 1,2-dichloroethane produced by oxychlorination and chlorination is purified and converted to vinyl chloride by dehydrochlorination, and in which one or more liquid waste streams containing chlorinated hydrocarbons boiling higher than 1,2-dichloroethane and also containing ferric chloride and/or other metallic substances are produced, the improvement comprising removing a substantial portion of the ferric chloride and/or other metallic substances from one or more of said waste streams by contacting said waste streams with dilute aqueous hydrochloric acid which contains from about 0.1 to about 10 percent by weight of hydrogen chloride, in a volume ratio of dilute acid to organic material contained in said waste stream of between about 1:1 and about 3:1 and separating the resulting aqueous and organic phases.

15. A process according to claim 14 in which the concentration of hydrogen chloride in the dilute aqueous solution is from about 2 to about 10 percent by weight.

16. A process according to claim 14 in which the volume ratio of dilute aqueous solution to organic material in the waste stream is about 1:1.

17. A process according to claim 14 further comprising filtering the liquid waste stream to remove solid particulate material before contacting it with the dilute aqueous hydrochloric acid.

18. A process according to claim 14 further comprising passing the mixture of liquid waste stream and dilute aqueous hydrochloric acid through a filter and coalescer, prior to separation of the organic and aqueous phases.

19. A process according to claim 14 in which the liquid waste stream being treated comprises a purge stream drawn off from the ethylene chlorination reactor.

20. A process according to claim 14 in which the waste stream comprises a bottoms product from a 1,2-dichloroethane/heavy ends distillation column.

21. A process according to claim 14 in which the waste stream comprises the residue from one or more concentration steps for separating 1,2-dichloroethane from high boiling impurities.

* * * * *